(12) United States Patent
Larson et al.

(10) Patent No.: US 7,107,994 B2
(45) Date of Patent: Sep. 19, 2006

(54) MEDICAL ARM SECURING DEVICE

(76) Inventors: Donald O. Larson, Box 223, Audubon, MN (US) 56511; Ryan L. Anderson, 1146 Linden La., Detroit Lakes, MN (US) 56501

( * ) Notice: Subject to any disclaimer, the term of this patent is extended or adjusted under 35 U.S.C. 154(b) by 136 days.

(21) Appl. No.: 10/632,460

(22) Filed: Jul. 31, 2003

(65) Prior Publication Data

US 2005/0022825 A1    Feb. 3, 2005

(51) Int. Cl.
*A61F 5/37* (2006.01)
(52) U.S. Cl. ..................................... 128/879
(58) Field of Classification Search ............... 128/869, 128/878, 879; 602/21, 22
See application file for complete search history.

(56) References Cited

U.S. PATENT DOCUMENTS

| | | | |
|---|---|---|---|
| 1,219,453 A | 3/1917 | Hansen | |
| 3,234,623 A | 2/1966 | Rector | 27/21 |
| 3,345,656 A | 10/1967 | Steinman | 5/327 |
| 3,474,781 A | 10/1969 | Gaylord, Jr. | 128/134 |
| 3,861,666 A | 1/1975 | Nishiyama et al. | 269/328 |
| 4,351,169 A * | 9/1982 | Plymale | 70/16 |
| 4,469,096 A * | 9/1984 | Rivadeneyra | 128/879 |
| 4,662,366 A | 5/1987 | Tari | 128/134 |
| 4,683,601 A | 8/1987 | Lagin | 5/431 |
| 4,741,051 A * | 5/1988 | Bible | 2/158 |
| 5,031,641 A * | 7/1991 | Upton | 128/879 |
| 5,088,158 A * | 2/1992 | Burkholder | 24/16 PB |
| 5,329,679 A | 7/1994 | Rojdev | 27/13 |
| 5,349,966 A * | 9/1994 | Garcia | 128/879 |
| 5,363,523 A | 11/1994 | Blackburn | 5/630 |
| 5,518,010 A * | 5/1996 | Dodge | 128/869 |
| 5,549,121 A | 8/1996 | Vinci | 128/878 |
| 6,073,631 A * | 6/2000 | Wilhelmy | 128/878 |
| 6,101,650 A | 8/2000 | Omdal et al. | 5/623 |
| 6,379,206 B1 * | 4/2002 | Wallasch | 441/80 |

* cited by examiner

*Primary Examiner*—Henry Bennett
*Assistant Examiner*—Camtu Nguyen

(57) ABSTRACT

A medical arm securing device for temporarily securing the arms of an immobile person in an accessible position. The medical arm securing device includes a main member, and a first slot and a second slot extending into the main member. The slots receive the wrists of an immobile patient and prevent the arms from falling to the sides. A securing slot extends into a bottom portion of the main member for attaching to a strap. A plurality of notches preferably extend into the front and rear ends of the main member for selectively receiving a band member.

11 Claims, 6 Drawing Sheets

MEDICAL ARM SECURING DEVICE

CROSS REFERENCE TO RELATED APPLICATIONS

Not applicable to this application.

Statement Regarding Federally Sponsored Research or Development

Not applicable to this application.

BACKGROUND OF THE INVENTION

1. Field of the Invention

The present invention relates generally to arm support devices and more specifically it relates to a medical arm securing device for temporarily securing the arms of an immobile person in an accessible position.

2. Description of the Related Art

Long backboards (LBB) have been in use for years for transporting an immobile patient (e.g. non-responsive, paralyzed, etc.). FIG. 6 of the drawings illustrates an exemplary long backboard that is utilized to transport immobile patients.

The main problem with conventional long backboards is that the patient's arms are prone to falling to the sides of the long backboard while transporting the patient. Arms of a patient hanging downwardly to the sides of the long backboard are prone to injury and make moving the patient difficult (e.g. narrow doorways, staircases, etc.).

To reduce movement of the arms, the securing straps of the long backboard are often times utilized to secure the arms of the patient in a desired position. However, the securing straps make it difficult to access the arms for medical personnel for performing medical tests/procedures thereby requiring loosening or removal of the securing strap. Loosening or removing the securing strap allows the arms to fall to the sides of the long backboard and also places the patient under an increased risk of accidentally falling from the long backboard while being transported.

While these devices may be suitable for the particular purpose to which they address, they are not as suitable for temporarily securing the arms of an immobile person in an accessible position. Conventional long backboards do not allow for convenient securing of the arms of a patient.

In these respects, the medical arm securing device according to the present invention substantially departs from the conventional concepts and designs of the prior art, and in so doing provides an apparatus primarily developed for the purpose of temporarily securing the arms of an immobile person in an accessible position.

BRIEF SUMMARY OF THE INVENTION

In view of the foregoing disadvantages inherent in the known types of arm securing devices now present in the prior art, the present invention provides a new medical arm securing device construction wherein the same can be utilized for temporarily securing the arms of an immobile person in an accessible position.

The general purpose of the present invention, which will be described subsequently in greater detail, is to provide a new medical arm securing device that has many of the advantages of the arm securing devices mentioned heretofore and many novel features that result in a new medical arm securing device which is not anticipated, rendered obvious, suggested, or even implied by any of the prior art arm securing devices, either alone or in any combination thereof.

To attain this, the present invention generally comprises a main member, and a first slot and a second slot extending into the main member. The slots receive the wrists of an immobile patient and prevent the arms from falling to the sides. A securing slot extends into a bottom portion of the main member for attaching to a strap. A plurality of notches preferably extend into the front and rear ends of the main member for selectively receiving a band member.

There has thus been outlined, rather broadly, the more important features of the invention in order that the detailed description thereof may be better understood, and in order that the present contribution to the art may be better appreciated. There are additional features of the invention that will be described hereinafter and that will form the subject matter of the claims appended hereto.

In this respect, before explaining at least one embodiment of the invention in detail, it is to be understood that the invention is not limited in its application to the details of construction and to the arrangements of the components set forth in the following description or illustrated in the drawings. The invention is capable of other embodiments and of being practiced and carried out in various ways. Also, it is to be understood that the phraseology and terminology employed herein are for the purpose of the description and should not be regarded as limiting.

A primary object of the present invention is to provide a medical arm securing device that will overcome the shortcomings of the prior art devices.

A second object is to provide a medical arm securing device for temporarily securing the arms of an immobile person in an accessible position.

Another object is to provide a medical arm securing device that allows medical personnel to access the arms and hands of a patient for medical procedures and tests without requiring removal of the arms from the securing apparatus.

An additional object is to provide a medical arm securing device that allows for quick, easy and efficient securing of an immobile patient's arms.

A further object is to provide a medical arm securing device that may be utilized by various types of medical personnel.

Another object is to provide a medical arm securing device that is easily sanitized after being utilized.

A further object is to provide a medical arm securing device that does not require straps or fasteners to secure the arms of an immobile patient.

Other objects and advantages of the present invention will become obvious to the reader and it is intended that these objects and advantages are within the scope of the present invention.

To the accomplishment of the above and related objects, this invention may be embodied in the form illustrated in the accompanying drawings, attention being called to the fact, however, that the drawings are illustrative only, and that changes may be made in the specific construction illustrated and described within the scope of the appended claims.

BRIEF DESCRIPTION OF THE DRAWINGS

Various other objects, features and attendant advantages of the present invention will become fully appreciated as the same becomes better understood when considered in conjunction with the accompanying drawings, in which like reference characters designate the same or similar parts throughout the several views, and wherein.

DETAILED DESCRIPTION OF THE INVENTION

A. Overview

Figure 1:
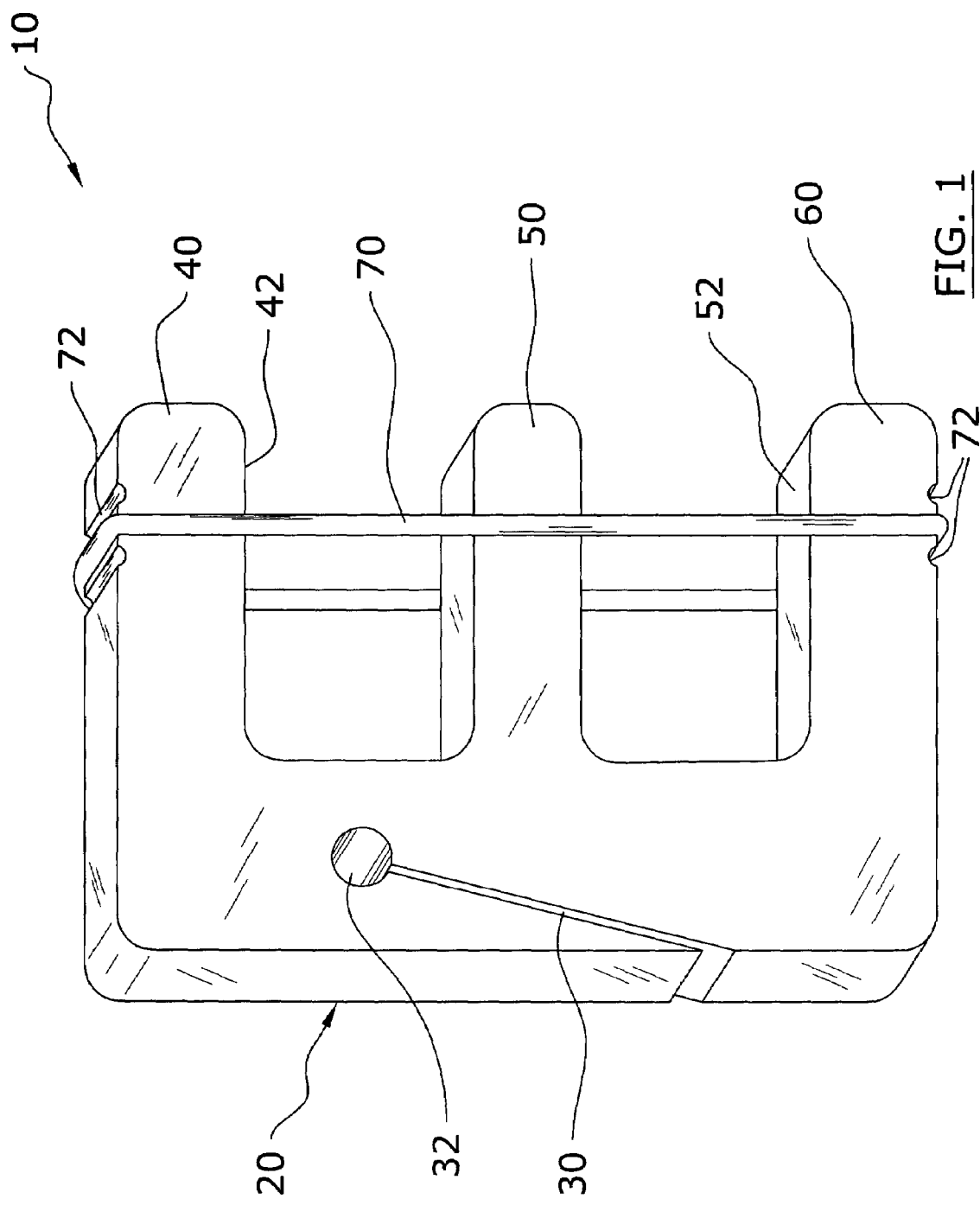
FIG. 1 is an upper perspective view of the present invention.

Turning now descriptively to the drawings, in which similar reference characters denote similar elements throughout the several views, FIGS. 1 through 6 illustrate a medical arm securing device 10, which comprises a main member 20, and a first slot 42 and a second slot 52 extending into the main member 20. The slots 42, 52 receive the wrists of an immobile patient 16 and prevent the arms from falling to the sides. A securing slot 30 extends into a bottom portion of the main member 20 for attaching to a strap 12. A plurality of notches 72 preferably extend into the front and rear ends of the main member 20 for selectively receiving a band member 70.

B. Main Member

The main member 20 is preferably an elongate flat structure as shown in FIGS. 1 through 6 of the drawings. The main member 20 may have various shapes, sizes and structure other than illustrated in the attached drawings.

The main member 20 has a rear portion that is positionable adjacent an immobile patient 16. The rear portion of the main member 20 is preferably straight or formed to fit adjacent to the patient 16 as shown in FIG. 4 of the drawings.

The main member 20 is preferably comprised of a nonporous material that allows for easy sanitizing of the main member 20 after usage on an immobile patient 16. The main member 20 may be comprised of various materials such as but not limited to metal, plastic, composite and the like.

Figure 2:
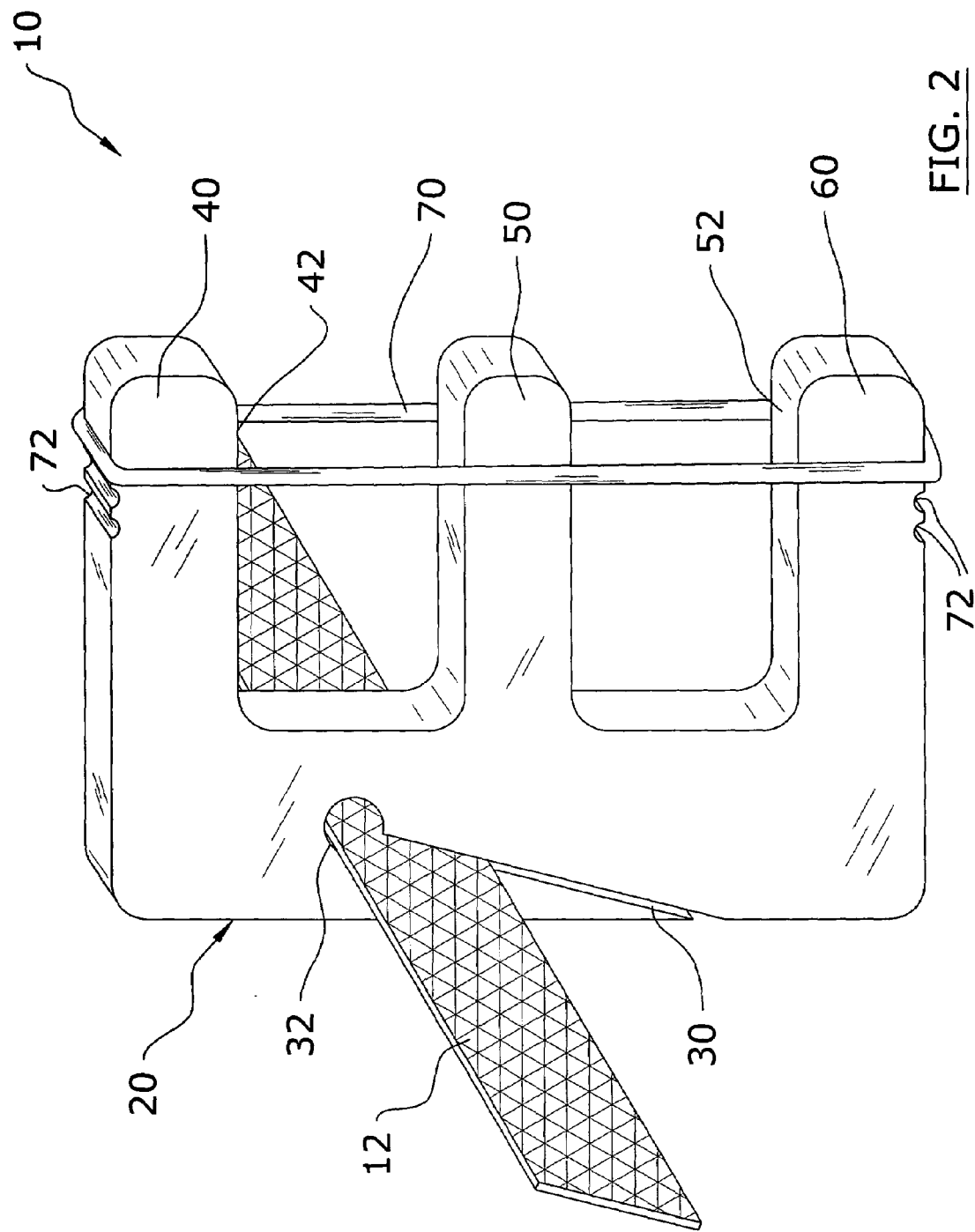
FIG. 2 is a first upper perspective view of the present invention attached to a strap.
Figure 3:
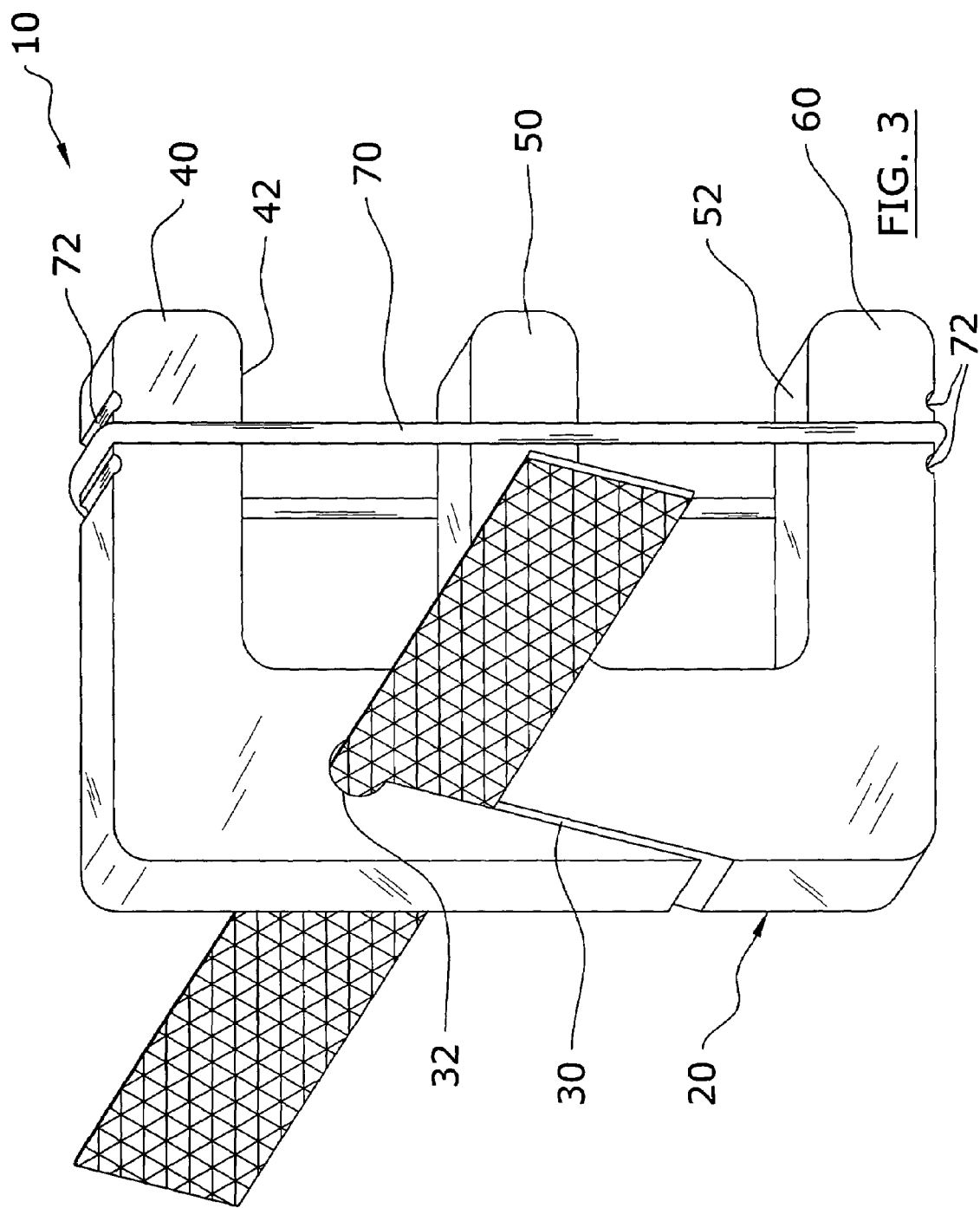
FIG. 3 is a second upper perspective view of the present invention attached to a strap.
Figure 4:
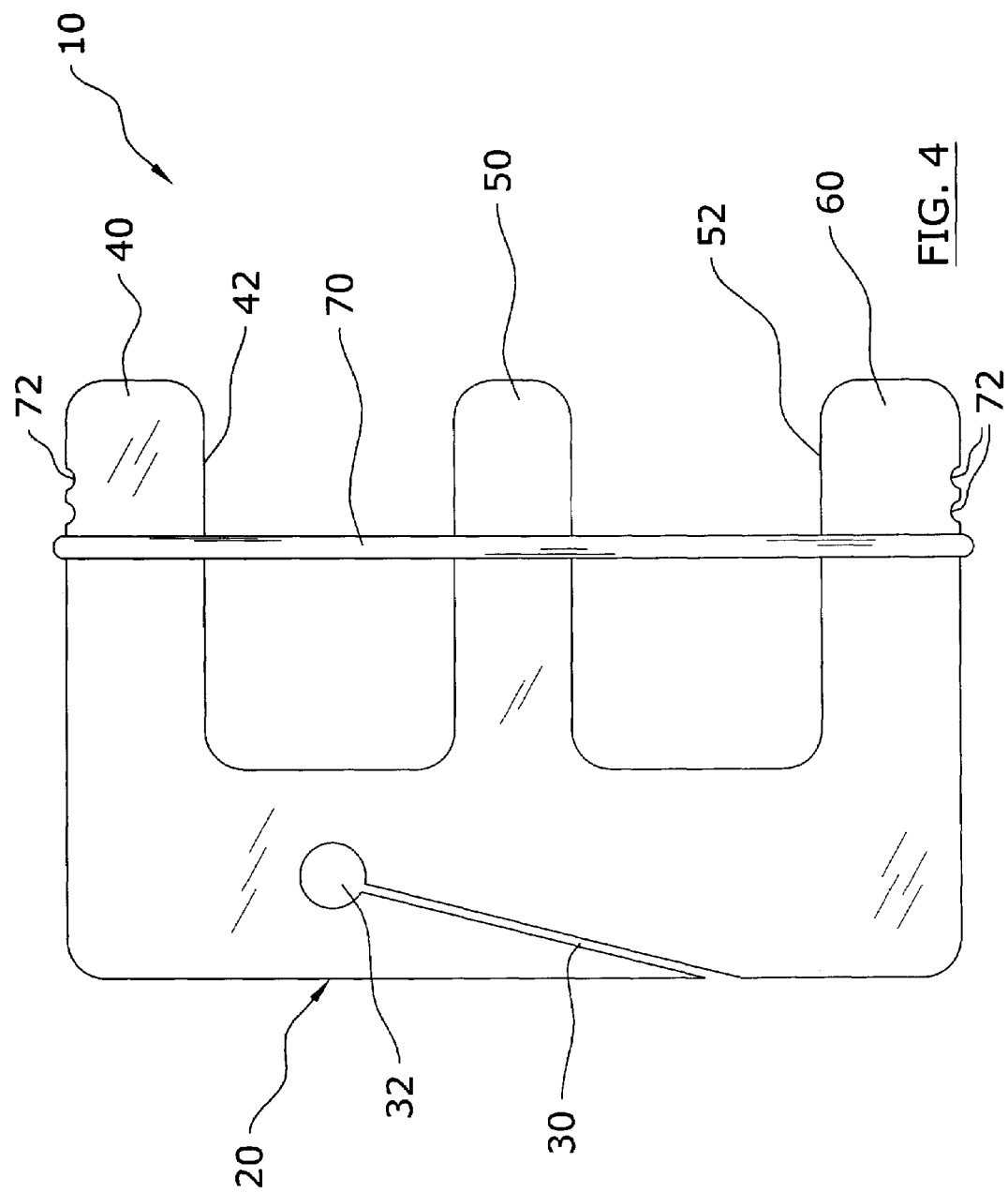
FIG. 4 is a side view of the present invention.
Figure 5:
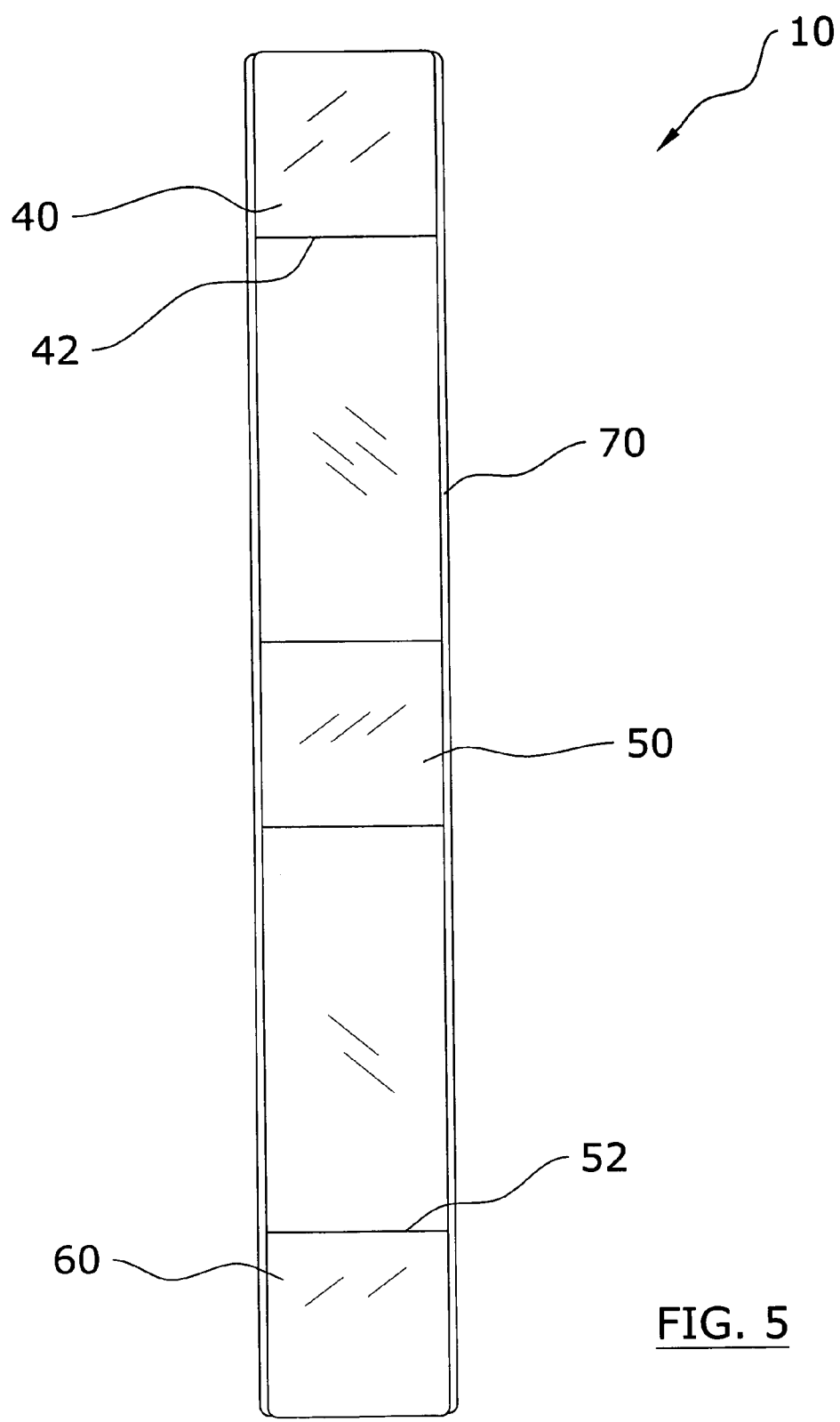
FIG. 5 is a top view of the present invention.

As best illustrated in FIG. 4 of the drawings, a securing slot 30 preferably extends into the lower portion of the main member 20 for removably receiving a strap 12. The securing slot 30 extends a sufficient distance for receiving at least a significant portion of a strap 12 utilized upon a long backboard 14 or the belt of a patient 16 as shown in FIGS. 2 and 3 of the drawings. A cutout 32 preferably extends into an inner end of the securing slot 30 for catchably receiving the strap 12.

As further shown in FIG. 4 of the drawings, the securing slot 30 is preferably straight and extends into the main member 20 at an angle. The angle is preferably less than forty-five degrees as shown in FIG. 4 of the drawings.

C. Slots 42, 52

As shown in FIGS. 1 through 5 of the drawings, a first slot 42 extends into an upper portion of the main member 20 for receiving a first arm 40 of a patient 16. A second slot 52 extends into the upper end of the main member 20 near the first slot 42 for receiving a second arm 50 of a patient 16.

The slots 42, 52 are preferably the same size and shape, however variations may exist between the slots 42, 52. The slots 42, 52 each have a depth and width sufficient for receiving the wrists of a patient 16. The slots 42, 52 may have rounded corners to prevent injury to the patient 16 during transport.

The slots 42, 52 are preferably substantially parallel to one another as further shown in FIG. 4 of the drawings. The slots 42, 52 form a first arm 40, a second arm 50 and a third arm 60 as further shown in FIG. 4 of the drawings. The arms are substantially parallel to one another and the main member 20 with the slots 42, 52 has an E-shaped structure as best shown in FIG. 4 of the drawings. Various other configurations may be utilized to achieve a similar structure and function.

D. Notches and Band Member

A plurality of notches 72 preferably extending into the opposing ends of the main member 20 as shown in FIGS. 1 through 4 of the drawings. The notches 72 may have various cross sectional shapes, but preferably are formed for securing receiving a portion of a band member 70.

The band member 70 is preferably comprised of a circular and resilient structure that is able to stretch over the main member 20 for engagement with the opposing notches 72. The band member 70 retains the arms of the patient 16 within the slots 42, 52.

E. Operation

Figure 6:
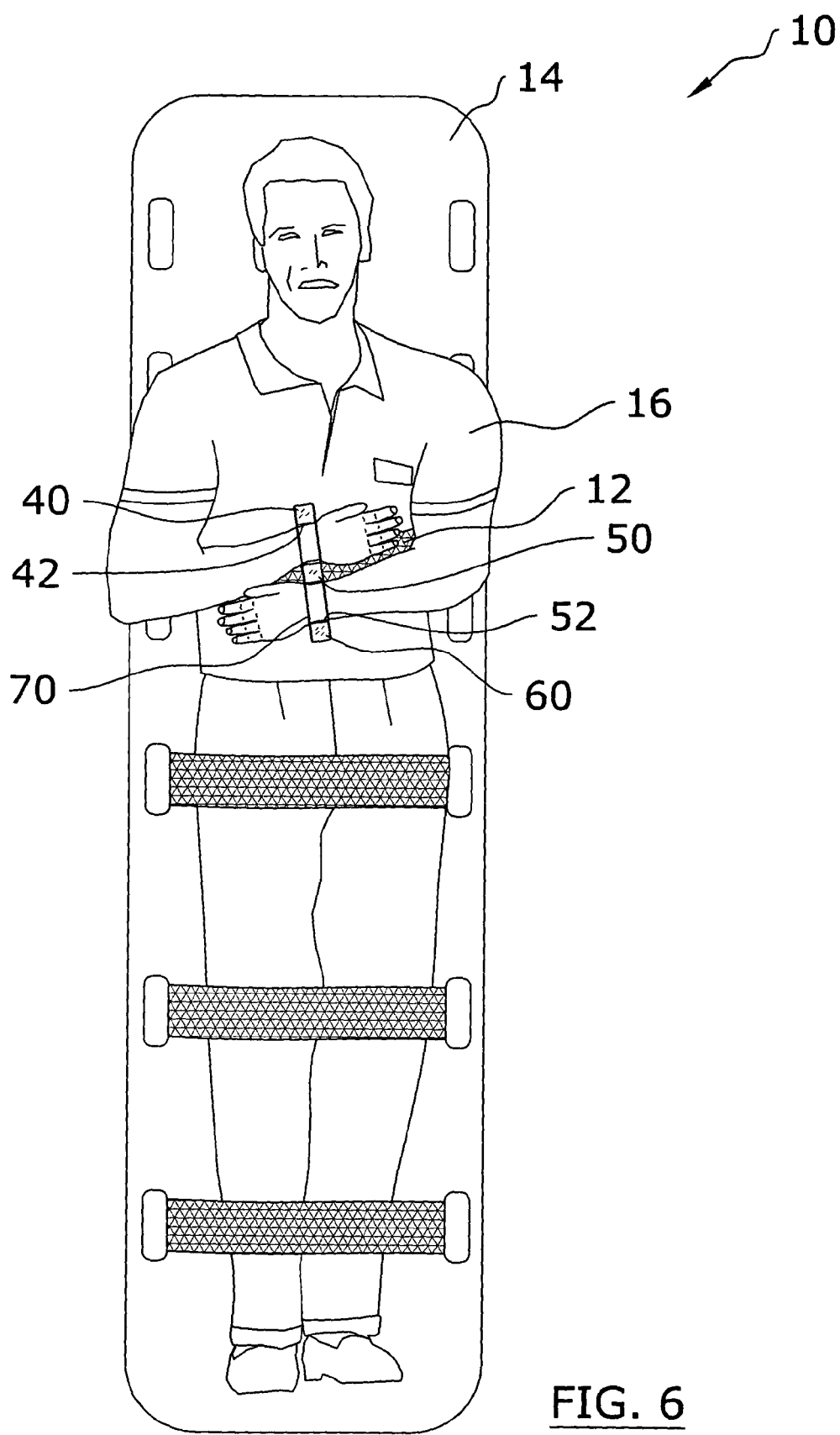
FIG. 6 is a top view of the present invention securing the arms of a patient.

In use, a patient 16 is first positioned upon a long backboard 14 and then secured using straps as shown in FIG. 6 of the drawings. The present invention is then positioned on the chest or abdomen of the patient 16 with the longitudinal axis of the main member 20 substantially parallel to the longitudinal axis of the patient 16. The main member 20 is preferably attached to one of the straps attached to the long backboard 14 by positioning the strap 12 within the securing slot 30 as shown in FIGS. 2 and 3 of the drawings.

The medical personnel then place a first arm 40 of the patient 16 into the first slot 42 of the main member 20 and a second arm 50 of the patient 16 into the second slot 52 of the main member 20 as shown in FIG. 6 of the drawings. The arms of the patient 16 are substantially parallel to one another when positioned within the slots 42, 52. If the arms of the patient 16 begin to fall outwardly, the arms bind within the main member 20 and are limited in their respective movement.

To ensure that the arms are not accidentally removed from the slots 42, 52 during transportation, the band member 70 may be secured upon the main member 20 in a desired position. The band member 70 is positioned within the notches 72 that correspond to the size of the arms to limit movement of the arms within the slots 42, 52. Medical personnel are then able to perform medical tests and medical procedures on the arms of the patients without obstruction.

The above-stated procedure is simply reversed to remove the arms of the patient 16 from the present invention. After usage, the main member 20 may be positioned within a sanitizing unit for usage on another patient 16. Alternatively, the present invention may be disposed of and replaced with a new replacement.

As to a further discussion of the manner of usage and operation of the present invention, the same should be apparent from the above description. Accordingly, no further discussion relating to the manner of usage and operation will be provided.

With respect to the above description then, it is to be realized that the optimum dimensional relationships for the parts of the invention, to include variations in size, materials, shape, form, function and manner of operation, assembly and use, are deemed to be within the expertise of those skilled in the art, and all equivalent structural variations and relationships to those illustrated in the drawings and described in the specification are intended to be encompassed by the present invention.

Therefore, the foregoing is considered as illustrative only of the principles of the invention. Further, since numerous modifications and changes will readily occur to those skilled in the art, it is not desired to limit the invention to the exact construction and operation shown and described, and accordingly, all suitable modifications and equivalents may be resorted to, falling within the scope of the invention.

We claim:

1. A medical arm securing device for securing the arms of an immobile patient, comprising:
    a main member;
    a first slot extending into an upper portion of said main member;
    a second slot extending into said upper portion of said main member, wherein said slots receive the wrists of an immobile patient, and wherein said second slot is substantially parallel to said first slot;
    a plurality of notches on opposing ends of said main member; and
    a band member positionable within selected said notches.

2. The medical arm securing device of claim 1, wherein said slots are substantially parallel to one another.

3. The medical arm securing device of claim 1, wherein said slots form a first arm, a second arm and a third arm.

4. The medical arm securing device of claim 3, wherein said arms are substantially parallel to one another.

5. The medical arm securing device of claim 4, wherein said main member has a rear portion that is positionable adjacent an immobile patient.

6. The medical arm securing device of claim 1, wherein said main member is comprised of a non-porous material.

7. The medical arm securing device of claim 1, including a securing slot extending into a lower portion of said main member for removably receiving a strap.

8. The medical arm securing device of claim 7, including a cutout at an inner end of said securing slot.

9. The medical arm securing device of claim 7, wherein said securing slot is straight and extends into said main member at an angle.

10. The medical arm securing device of claim 1, wherein said main member with said slots has an E-shape.

11. A medical arm securing device for securing the arms of an immobile patient, comprising:
    a main member;
    a first slot extending into an upper portion of said main member;
    a second slot extending into said upper portion of said main member, wherein said slots receive the wrists of an immobile patient;
    a plurality of notches on opposing ends of said main member;
    a band member positionable within selected said notches.
    wherein said slots are substantially parallel to one another;
    wherein said slots form a first arm, a second arm and a third arm within said main member;
    wherein said arms are substantially parallel to one another;
    wherein said main member has a rear portion that is positionable adjacent an immobile patient;
    wherein said main member is comprised of a non-porous material;
    a securing slot extending into a lower portion of said main member for removably receiving a strap; and
    a cutout at an inner end of said securing slot;
    wherein said securing slot is straight and extends into said main member at an angle;
    wherein said main member with said slots has an E-shape.

* * * * *